US009254001B2

(12) United States Patent
Hege Byrd et al.

(10) Patent No.: US 9,254,001 B2
(45) Date of Patent: Feb. 9, 2016

(54) TOBACCO-DERIVED COMPONENTS AND MATERIALS

(75) Inventors: Crystal Dawn Hege Byrd, Lexington, NC (US); Anthony Richard Gerardi, Winston-Salem, NC (US); Michael Francis Dube, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 1305 days.

(21) Appl. No.: 13/095,277

(22) Filed: Apr. 27, 2011

(65) Prior Publication Data

US 2012/0272976 A1 Nov. 1, 2012

(51) Int. Cl.
- *A24B 15/34* (2006.01)
- *C07H 13/02* (2006.01)
- *A24B 15/24* (2006.01)
- *A24B 15/30* (2006.01)

(52) U.S. Cl.
CPC ............... *A24B 15/24* (2013.01); *A24B 15/30* (2013.01)

(58) Field of Classification Search
CPC ..................................... A24B 15/241
USPC ......................... 131/275, 276, 352
See application file for complete search history.

(56) References Cited

U.S. PATENT DOCUMENTS

| | | | |
|---|---|---|---|
| 4,144,895 A | 3/1979 | Fiore | |
| 4,150,677 A | 4/1979 | Osborne, Jr. et al. | |
| 4,267,847 A | 5/1981 | Reid | |
| 4,289,147 A | 9/1981 | Wildman et al. | |
| 4,351,346 A | 9/1982 | Brummer et al. | |
| 4,359,059 A | 11/1982 | Brummer et al. | |
| 4,433,695 A | 2/1984 | Hall et al. | |
| 4,506,682 A | 3/1985 | Muller | |
| 4,517,385 A | 5/1985 | Light et al. | |
| 4,547,594 A | 10/1985 | Light et al. | |
| 4,589,428 A | 5/1986 | Keritsis | |
| 4,591,442 A | 5/1986 | Andrews | |
| 4,605,016 A | 8/1986 | Soga et al. | |
| 4,716,911 A | 1/1988 | Poulose et al. | |
| 4,727,889 A | 3/1988 | Niven, Jr. et al. | |
| 4,887,618 A | 12/1989 | Bernasek et al. | |
| 4,941,484 A | 7/1990 | Clapp et al. | |
| 4,967,771 A | 11/1990 | Fagg et al. | |
| 4,986,286 A | 1/1991 | Roberts et al. | |
| 4,992,106 A | 2/1991 | Christenson et al. | |
| 5,005,593 A | 4/1991 | Fagg et al. | |
| 5,018,540 A | 5/1991 | Grubbs et al. | |
| 5,060,669 A | 10/1991 | White et al. | |
| 5,065,775 A | 11/1991 | Fagg | |
| 5,074,319 A | 12/1991 | White et al. | |
| 5,099,862 A | 3/1992 | White et al. | |
| 5,121,757 A | 6/1992 | White et al. | |
| 5,131,414 A | 7/1992 | Fagg et al. | |
| 5,131,415 A | 7/1992 | Munoz et al. | |
| 5,148,819 A | 9/1992 | Fagg | |
| 5,197,494 A | 3/1993 | Kramer | |
| 5,230,354 A | 7/1993 | Smith et al. | |
| 5,234,008 A | 8/1993 | Fagg | |
| 5,243,999 A | 9/1993 | Smith | |
| 5,301,694 A | 4/1994 | Raymond et al. | |
| 5,318,050 A | 6/1994 | Gonzalez-Parra et al. | |
| 5,343,879 A | 9/1994 | Teague | |
| 5,360,022 A | 11/1994 | Newton et al. | |
| 5,435,325 A | 7/1995 | Clapp et al. | |
| 5,445,169 A | 8/1995 | Brinkley et al. | |
| 5,891,501 A | 4/1999 | McKellip et al. | |
| 6,131,584 A | 10/2000 | Lauterbach | |
| 6,298,859 B1 | 10/2001 | Kierulff et al. | |
| 6,772,767 B2 | 8/2004 | Mua et al. | |
| 7,025,066 B2 | 4/2006 | Lawson et al. | |
| 7,337,782 B2 | 3/2008 | Thompson | |
| 2006/0283469 A1 | 12/2006 | Lipowicz | |
| 2007/0137663 A1 | 6/2007 | Taylor et al. | |
| 2008/0209586 A1* | 8/2008 | Nielsen et al. | 800/270 |
| 2008/0254149 A1 | 10/2008 | Havkin-Frenkel | |
| 2012/0192880 A1* | 8/2012 | Dube et al. | 131/275 |
| 2012/0192882 A1* | 8/2012 | Dube et al. | 131/332 |

FOREIGN PATENT DOCUMENTS

| | | |
|---|---|---|
| CN | 101 129 216 | 2/2008 |
| JP | 4 082896 | 3/1992 |
| JP | 5 186489 | 7/1993 |
| KR | 2006 0054786 | 5/2006 |

OTHER PUBLICATIONS

Coleman, III et al., "The Use of a Non-equilibrated Solid Phase Microextraction Method to Quantitatively Determine the Off-notes in Mint and other Essential Oils," *J. Sci Food Agric*, 2004, vol. 84, pp. 1223-1228.

Coleman, III et al., "Headspace Solid-Phase Microextraction Analysis of Artificial Flavors," *J. Sci Food Agric.*, 2005, vol. 85, pp. 2645-2654.

(Continued)

*Primary Examiner* — James Sanders
*Assistant Examiner* — Kimberly A Stewart
(74) *Attorney, Agent, or Firm* — Womble Carlyle Sandridge & Rice, LLP

(57) ABSTRACT

The invention provides a method of extracting and isolating certain compounds from tobacco. The resulting isolate can include more than 90% by weight of a given compound and can be used as a flavor component for tobacco material used in smoking articles and smokeless tobacco compositions. Exemplary compounds that may be present in the isolate according to the invention include, but are not limited to, solanone, neophytadiene, megastigmatrienone, β-damascenone, norsolanadione, cis-abienol, α-cembratrienediol, β-cembratrienediol, sucrose esters, and lutein.

34 Claims, No Drawings

(56) References Cited

OTHER PUBLICATIONS

Demole, et al. "A Chemical Study of *Burley* Tobacco Flavour (*Nicotiana tabacum* L.) Volatile to Medium-Volatile Constituents (b.p. < 84° /0.001 Torr," *Helv. Chim. Acta*, 1972, vol. 55, No. 6, pp. 1866-1882.

Ishikawa et al., "Water-Soluble Constituents of Dill," *Chem. Pharm. Bull.*, 2002, vol. 50, No. 4, pp. 501-507.

Johnson, et al. "The Structure, Chemistry, and Synthesis of Solanone. A New Anomalous Terpenoid Ketone from Tobacco," *J. Org. Chem.*, 1965, vol. 30, No. 9, pp. 2918-2921.

Kandra, et al. "Studies of the Site and Mode of Biosynthesis of Tobacco Trichome Exudate Components," *Arch Biochem Biophys.*, 1988, vol. 265, No. 2 pp. 425-432.

Ochiai, Ph,D., "Take Two," *Gerstel Solutions Worldwide*, 2006, No. 6, pp. 17-19.

Saito, et al. "Inhibitory effects of Cembratriene-4,6-diol Derivative on the Induction of Epstein-Barr Virus Early Antigen by 12-*O*-Tetradecanoylphorbol-13-acetate," *Agric. Biol. Chem.*, 1987, vol. 51, No. 3, pp. 941-943.

Severson, et al. "Isolation and Characterization of the Sucrose Esters of the Cuticular Waxes of Green Tobacco Leaf," *J. Agric. Food Chem.*, 1985, vol. 33, No. 5 pp. 870-875.

Still, et al. "Rapid Chromatographic Technique for Preparative Separations with Moderate Resolutions," *J. Org. Chem.*, 1978, vol. 43, No. 14, pp. 2923-2925

Ohya et al., "Sucrose Estes from the Surface Lipids of Nicotiana Cavicola," *Pytochemistry*, 1994, pp. 143-145, vol. 37, No. 1.

\* cited by examiner

US 9,254,001 B2

TOBACCO-DERIVED COMPONENTS AND MATERIALS

FIELD OF THE INVENTION

The present invention relates to products made or derived from tobacco, or that otherwise incorporate tobacco, and are intended for human consumption. Of particular interest are ingredients or components obtained or derived from plants or portions of plants from the *Nicotiana* species.

BACKGROUND OF THE INVENTION

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, $3^{rd}$ Ed., p. 43 (1990) and *Tobacco Production, Chemistry and Technology*, Davis et al. (Eds.) p. 346 (1999).

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. Appl. Pub. Nos. 2005/0244521 to Strickland et al. and 2009/0293889 to Kumar et al.; PCT WO 04/095959 to Arnarp et al.; PCT WO 05/063060 to Atchley et al.; PCT WO 05/004480 to Engstrom; PCT WO 05/016036 to Bjorkholm; and PCT WO 05/041699 to Quinter et al., each of which is incorporated herein by reference. See, for example, the types of smokeless tobacco formulations, ingredients, and processing methodologies set forth in U.S. Pat. No. 6,953,040 to Atchley et al. and U.S. Pat. No. 7,032,601 to Atchley et al., each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R.J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen, Skoal, SkoalDry, Rooster, Red Seal, Husky, and Revel by U.S. Smokeless Tobacco Co.; "taboka" by Philip Morris USA; Levi Garrett, Peachy, Taylor's Pride, Kodiak, Hawken Wintergreen, Grizzly, Dental, Kentucky King, and Mammoth Cave by Conwood Company, LLC; and Camel Orbs, Camel Sticks, and Camel Strips by R.J. Reynolds Tobacco Company.

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. See also, Leffingwell et al., *Tobacco Flavoring for Smoking Products*, R.J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; and U.S. Pat. No. 6,591,841 to White et al.; US Pat. Appl. Publication Nos. 2004/0173228 to Coleman, III and 2010/0037903 to Coleman, III et al., each of which is incorporated herein by reference.

The sensory attributes of smokeless tobacco can also be enhanced by incorporation of certain flavoring materials. See, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/

0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

There is a need in the art for flavorful compositions suitable for addition to smoking products or smokeless tobacco products to introduce desired characteristics. It would be desirable to provide a method for efficient extraction and isolation of such compositions.

SUMMARY OF THE INVENTION

The present invention provides a method of extracting and isolating various compounds from plants of the *Nicotiana* species. The method of the invention is selective for certain compounds that impart flavorful characteristics and/or compounds that degrade to produce compounds that impart flavorful characteristics to smoking articles and/or smokeless tobacco products. The invention also provides methods for processing these compounds and tobacco materials incorporating these compounds.

Thus, in one aspect, the present invention provides a method of extracting and isolating compounds from plants of the *Nicotiana* species. In certain embodiments, the method comprises receiving a plant material of the *Nicotiana* species; contacting the plant material with a solvent for a time and under conditions sufficient to extract one or more desired compounds from the plant material into the solvent; separating the solvent containing the one or more desired compounds from the extracted plant material; and purifying the solvent containing the one or more desired compounds to provide an isolate. In some embodiments, the isolate thus obtained comprises at least about 75 percent by weight of the one or more desired compounds. In certain embodiments, the one or more desired compounds are selected from the group consisting of solanone, neophytadiene, megastigmatrienone, β-damascenone, norsolanadione, cis-abienol, α-cembratrienediol, β-cembratrienediol, sucrose esters, lutein, degradation products thereof, and mixtures thereof.

In some embodiments, the plant material of the *Nicotiana* species is in a form selected from the group consisting of whole leaf, laminae, cut filler, volume expanded, stems, cut-rolled stems, cut-puffed stems, reconstituted tobacco, and particulate. In some embodiments, the plant material of the *Nicotiana* species is provided in green form or in cured form.

In certain embodiments, the solvent is methanol. The one or more desired compounds thus obtained can be, for example, selected from the group consisting of cis-abienol, α-cembratrienediol, β-cembratrienediol, sucrose esters, and lutein. In certain embodiments, the solvent is dry steam. The one or more desired compounds thus obtained can be, for example, selected from the group consisting of solanone, neophytadiene, megastigmatrienone, β-damascenone, and norsolanadione. When the solvent is dry steam, the contacting step can further comprise collecting a distillate. In some embodiments, the distillate can comprise a water layer and an oily layer and the solvent containing the one or more desired compounds can be selected from the group consisting of the oily layer, the water layer, and a waste stream generated from the distillation process.

In some embodiments, the purifying step comprises using preparative scale liquid chromatography. In certain embodiments, the purifying step comprises using flash chromatography. The purifying step can provide an isolate with a desired level of the one or more desired compounds, for example, greater than about 90% by weight or greater than about 95% by weight of the one or more desired compounds. In certain embodiments, the method further comprises adding the isolate to a tobacco composition adapted for use in a smoking article or a smokeless tobacco composition.

In some embodiments, the isolate can be further treated to provide one or more degradation products therefrom, wherein the treating comprises oxidation (i.e., treating with $H_2O_2$ or another oxidizing reagent) and/or heat treatment. As one example, the isolate can comprise lutein and the one or more degradation products can be selected from the group consisting of megastigmatrienone, beta-damascenone, and mixtures thereof. As another example, the isolate can comprise cis-abienol and the one or more degradation products can be selected from the group consisting of sclareolide, sclareol, ambroxide, and mixtures thereof.

In another aspect of the present invention is provided a method for providing a flavor material derived from a plant of the *Nicotiana* species for addition to a tobacco composition, the method comprising receiving a plant material of the *Nicotiana* species; contacting the plant material with a solvent for a time and under conditions sufficient to extract one or more desired compounds from the plant material into the solvent; separating the solvent containing the one or more desired compounds from the extracted plant material; purifying the solvent containing the one or more compounds to provide an isolate comprising at least about 75% by weight of the one or more desired compounds, the one or more desired compounds being selected from the group consisting of solanone, neophytadiene, megastigmatrienone, β-damascenone, norsolanadione, cis-abienol, α-cembratrienediol, β-cembratrienediol, sucrose esters, lutein, degradation products thereof, and mixtures thereof; and adding the isolate to a tobacco composition adapted for use in a smoking article or a smokeless tobacco composition.

Various modifications can be made to the method of providing a flavor material, as noted above for the method of extracting and isolating compounds. For example, the plant material and solvent used can be varied, and various additional treatment methods can be used in combinations with the inventive method.

The isolate can be added to the tobacco composition in a variety of ways. For example, the isolate can be added the form of a casing formulation or a top dressing formulation applied to tobacco strip or in the form of a component of a reconstituted tobacco material. In certain embodiments, the tobacco composition comprises a tobacco material adapted for use in a smoking article. In such embodiments, the amount of isolate in the tobacco composition can be, for example, between about 5 ppm and about 5 percent by weight, based on the total dry weight of the tobacco material in the smoking article. In certain embodiments, the tobacco composition comprises a tobacco material adapted for use in a smokeless tobacco product. In such embodiments, the amount of isolate in the tobacco composition can be, for example, between about 5 ppm and about 5 percent by weight, based on the total dry weight of the tobacco material in the smokeless tobacco product.

In another aspect of the present invention is provided an isolate from a plant of the *Nicotiana* species or components thereof, wherein the isolate comprises at least about 75 percent by weight of a compound selected from the group consisting of solanone, neophytadiene, megastigmatrienone, β-damascenone, norsolanadione, cis-abienol, α-cembratrienediol, β-cembratrienediol, sucrose esters, lutein, and degradation products thereof, and mixtures thereof. In some embodiments, the isolate comprises greater than about 90% by weight or greater than about 95% by weight of the one or more desired compounds. In some embodiments are provided tobacco compositions comprising the isolate for use in smoking articles or smokeless tobacco compositions.

DETAILED DESCRIPTION OF THE PREFERRED EMBODIMENTS

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Various representative types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Exemplary *Nicotiana* species include are *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis subsp. Hersperis, N. pauciflora, N. petunioides, N. quadrivalvis, N. repanda, N. rotundifolia, N. solanifolia* and *N. spegazzinii*.

*Nicotiana* species can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al.

For the preparation of smokeless and smokable tobacco products, it is typical for harvested plants of the *Nicotiana* species to be subjected to a curing process. Descriptions of various types of curing processes for various types of tobaccos are set forth in *Tobacco Production, Chemistry and Technology*, Davis et al. (Eds.) (1999). Exemplary techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing. Preferably, harvested tobaccos that are cured are then aged.

At least a portion of the plant of the *Nicotiana* species (e.g., at least a portion of the tobacco portion) can be employed in an immature form. That is, the plant, or at least one portion of that plant, can be harvested before reaching a stage normally regarded as ripe or mature. As such, for example, tobacco can be harvested when the tobacco plant is at the point of a sprout, is commencing leaf formation, is commencing flowering, or the like. At least a portion of the plant of the *Nicotiana* species (e.g., at least a portion of the tobacco portion) can be employed in a mature form. That is, the plant, or at least one portion of that plant, can be harvested when that plant (or plant portion) reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position.

In accordance with the present invention, a tobacco product incorporates tobacco that is combined with one or more compounds extracted and/or isolated from a plant of the *Nicotiana* species in green form or cured form. At least a portion of the tobacco product can comprise compounds removed from the *Nicotiana* plant (e.g., by extraction, distillation, or other types of processing techniques). In some embodiments, at least a portion of the tobacco product can be composed of degradation products derived from these compounds, such as compounds collected after subjecting the plants to chemical reaction or after subjecting compounds or mixtures thereof isolated from *Nicotiana* plants to chemical reaction (e.g., acid/base reaction conditions, oxidation conditions, enzymatic treatment, and/or heat treatment).

The *Nicotiana* species can be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be employed. For example, virtually all of the plant (e.g., the whole plant) can be harvested, and employed as such. Alternatively, various parts or pieces of the plant can be harvested or separated for further use after harvest. For example, the leaves, stem, stalk, and various combinations thereof, can be isolated for further use or treatment. The plant material of the invention may thus comprise an entire plant or any portion of a plant of the *Nicotiana* species.

The post-harvest processing of the plant or portion thereof can vary. After harvest, the plant or portion thereof can be used in a green form (e.g., the plant or portion thereof can be used without being subjected to any curing process). For example, the plant or portion thereof can be used without being subjected to significant storage, handling or processing conditions. In certain situations, it is preferable that the plant or portion thereof be used virtually immediately after harvest. Alternatively, for example, a plant or portion thereof in green form can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use.

The harvested plant or portion thereof can be physically processed. The plant or portion thereof can be separated into individual parts or pieces (e.g., the leaves can be removed from the stems, and/or the stems and leaves can be removed from the stalk. The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

The plant of the *Nicotiana* species or portions thereof can be subjected to other types of processing conditions. For example, components can be separated from one another or otherwise fractionated into chemical classes or mixtures of individual compounds. Typical separation processes can include one or more process steps (e.g., solvent extraction using polar solvents, organic solvents, or supercritical fluids), chromatography, distillation, filtration, recrystallization, and/or solvent-solvent partitioning. Exemplary extraction and separation solvents or carriers include water, alcohols (e.g., methanol or ethanol), hydrocarbons (e.g., heptane and hexane), diethyl ether, methylene chloride and supercritical carbon dioxide. Exemplary techniques useful for extracting components from *Nicotiana* species are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121, 757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230, 354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated herein by reference. See also, the types of separation techniques set forth in Brandt et al., *LC-GC Europe*, p. 2-5 (March, 2002) and Wellings, *A Practical Handbook of Preparative HPLC* (2006), which are incorporated herein by reference. In addition, the plant or portions thereof can be subjected to the types of treatments set forth in Ishikawa et al., *Chem. Pharm. Bull.*, 50, 501-507 (2002); Tienpont et al., *Anal. Bioanal. Chem.*, 373, 46-55 (2002); Ochiai, *Gerstel Solutions Worldwide*, 6, 17-19 (2006); Coleman, III, et al., *J. Sci. Food and Agric.*, 84, 1223-1228 (2004); Coleman, III et al., *J. Sci. Food and Agric.*, 85, 2645-2654 (2005); Pawliszyn, ed., *Applications of Solid Phase Microextraction, RSC Chromatography Monographs*, (Royal Society of Chemistry, UK) (1999); Sahraoui et al., *J. Chrom.*, 1210, 229-233 (2008); and U.S. Pat. No. 5,301,694 to Raymond et al., which are incorporated herein by reference.

In particular, in certain embodiments, one or more compounds of interest are extracted from a plant material of the *Nicotiana* species or a portion thereof by contacting the plant or portion thereof with a solvent under conditions (e.g., suitable pressure and temperature) sufficient to extract one or more desired compounds from the plant material. In some embodiments, the solvent is an organic solvent, such as methanol or hexanes. In other embodiments, the solvent is dry steam. Dry steam (also referred to as anhydrous steam) is steam having a minimal content of suspended water particles (i.e., moisture). For example, dry steam typically comprises less than about 5% water particles by weight or less than about 10% water particles by weight.

The temperature and pressure at which the extraction process is conducted can vary. However, in some embodiments, suitable extraction is achieved at ambient temperature and pressure. Further, the amount of time that the solvent is in contact with the tobacco material can vary. Typically, the solvent will remain in contact with the tobacco material for approximately two hours, although longer or shorter time periods can be used without departing from the invention.

Exemplary compounds of interest that can be present in the extract obtained according to the methods of the present invention include, but are not limited to, solanone, neophytadiene, megastigmatrienone, β-damascenone, norsolanadione, cis-abienol, α-cembratrienediol, β-cembratrienediol, sucrose esters, and/or lutein.

Further processing of the extracted product can be carried out in a number of ways. The method of further processing can depend on the compounds present in the extract and/or the type of solvent used in the extraction.

For example, where an organic solvent (e.g., methanol or hexanes) is used to extract one or more compounds from the tobacco material, the solvent brought into contact with the tobacco material can simply be filtered to remove particulate tobacco material and the filtrate can be concentrated.

Where dry steam is used to extract one or more compounds from the tobacco material, the dry steam is typically condensed following the contacting step to give a steam distillate.

In certain embodiments, this distillation method is conducted on various mixtures of cured tobacco materials. For example, in one embodiment, a mixture of flue-cured, burley, and Oriental tobaccos is used. Methods used for the production of essential oils can be used herein to distill compounds of interest from tobacco plants or portions thereof. For exemplary steam distillation processes and conditions that can be used or modified for use to provide compounds of interest from tobacco plants or portions thereof according to the present invention, see for example, U.S. Pat. No. 5,891,501 to McKellip et al., which is incorporated herein by reference. The type of apparatus used to process the material in this way can be, for example, the type traditionally employed for the isolation of peppermint oils. In certain embodiments, the steam distillate comprises a water condensate layer and an oily layer that can be separated from each other.

The oily layer thus obtained from the tobacco material typically comprises one or more compounds of interest (e.g., neophytadiene, solanone, megastigmatrienone isomers, β-damascenone, and norsolanadione). In certain embodiments, the oily layer advantageously is rich in flavor compounds, including one or more of the compounds of interest noted above, and is essentially alkaloid free. For example, in certain embodiments, the oily layer contains less than about 15% by weight, less than about 10% by weight, less than about 5% by weight, less than about 2% by weight, less than about 1% by weight, or less than about 0.5% by weight alkaloids. The percentages of other compounds present in the oily layer can vary, depending for example, on the type of tobacco subjected to distillation by the methods provided herein.

The waste water resulting from the distillation process may, in certain embodiments, also comprise compounds of interest (e.g., including, but not limited to, those compounds of interest noted to be present in the oily layer). These compounds are believed to be present both in the oily layer and in the water because the distillation process can provide certain compounds with notable solubility in water. Therefore, in some embodiments, compounds of interest are isolated from the waste water produced by the distillation process. For example, in some embodiments, flavor compounds and/or nicotine are present in the waste water. It is noted that the percentage of various volatile and semi-volatile compounds in the waste water varies as a function of time. Thus, various fractions of the waste water can be collected separately to provide solutions containing higher percentages of certain compounds. Accordingly, the invention provides for the extraction of desired compounds by distillation, wherein the desired compounds are provided in the oily layer of the distillate, the water layer of the distillate, and/or in the waste water produced during the distillation process.

Various compounds or mixtures of compounds from the Nicotiana plant or portions thereof can be isolated by the methods provided herein. As used herein, an "isolated component," or "plant isolate," is a compound or complex mixture of compounds separated from a plant of the Nicotiana species or a portion thereof. The isolated component can be a single compound, a homologous mixture of similar compounds (e.g., isomers of a flavor compound), or a heterologous mixture of dissimilar compounds (e.g., a complex mixture of various compounds of different types, preferably having desirable sensory attributes). Tobacco material that has been subjected to the extraction methods described herein may be further processed, e.g., to extract one or more additional compounds therefrom. See, for example, US Patent App. Publ. No. 2008/0254149 to Havkin-Frenkel, which is incorporated herein by reference.

According to the present invention, a variety of compounds having distinctive flavor and aroma characteristics can be extracted and/or isolated from plants of the Nicotiana species. Certain of those compounds can be considered to be volatile under normal ambient conditions of temperature, humidity and air pressure. Preferred compounds exhibit positive sensory attributes at relatively low concentrations. Examples of the types of compounds that can be present in Nicotiana plants and extracted and isolated by the methods described herein include solanone, neophytadiene, megastigmatrienone, β-damascenone, norsolanadione, cis-abienol, α-cembratrienediol, β-cembratrienediol, sucrose esters, and/or lutein.

Cis-abienol is a major labdanoid in the green leaf of tobaccos. For example, cis-abienol is commonly found in Oriental tobaccos.

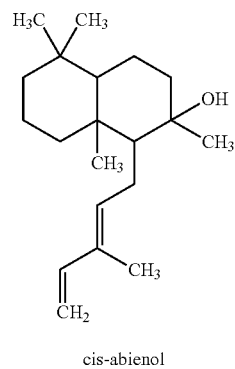 [SMILES: C=C/C(C)=C/CC1C(C)(O)CCC2C(C)(C)CCCC21C]

cis-abienol

During air- and sun-curing of green Oriental tobaccos, the concentration of cis-abienol typically decreases significantly, as numerous labdanoid degradation products are formed. The labdanoid degradation products are structurally similar to cis-abienol, and include, for example, sclareolide, sclareol, and ambroxide. These degradation products are known to impart cedar characteristics to tobacco products containing Oriental tobaccos.

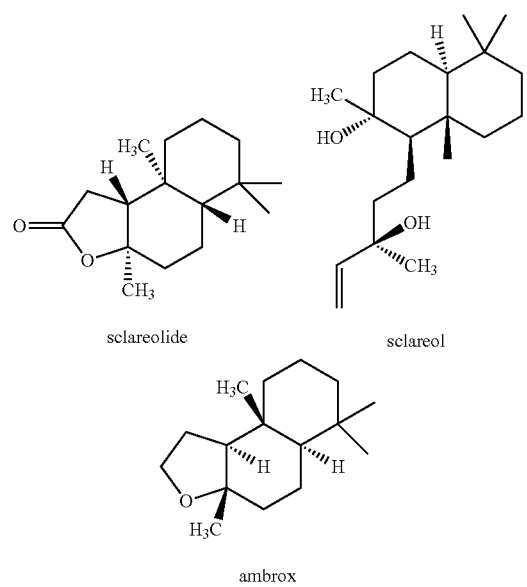

sclareolide         sclareol ambrox

Isolated cis-abienol may find a number of applications in smoking products and/or smokeless tobacco products. In some embodiments, isolated cis-abienol is degraded by various means and the degradation products can be used in smoking products and/or smokeless tobacco products. For example, in certain embodiments, isolated cis-abienol and/or degradation products thereof find use as tobacco-derived, natural flavor materials (e.g., Turkish replacement flavor material) or Oriental tobacco replacements. In some embodiments, cis-abienol and/or degradation products are used for therapeutic or neutriceutical applications. For example, labdanoid compounds have shown anti-cancer activity. See, for example, Jung et al., *Bioorg. Med. Chem. Lett.* 8: 3295-98 (1998), which is incorporated herein by reference. In some embodiments, cis-abienol is used as a substrate in the preparation of other compounds. For example, it has been used as a substrate in the synthesis of weidendiols, which are cholesterol ester transfer protein inhibitors that may reduce the risk of atherosclerosis. See, for example, Barrero et al., *Tetrahedron* 54: 5635-5650 (1998), which is incorporated herein by reference.

Cembratrienediols (e.g., α-2,7,11-cembratriene-4,6-diol and β-2,7,11-cembratriene-4,6-diol) are found in high quantities in the leaf and flower of *Nicotiana tabacum*. Biodegradation of these compounds during curing of tobacco leaves results in the formation of a range of flavor compounds. Cembratrienediols have a structure as depicted below.

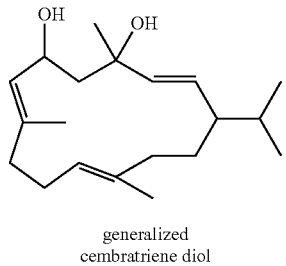 [SMILES: C/C1=C\C(O)CC(C)(O)/C=C/C(C(C)C)CC/C(C)=C/CC1]

generalized
cembratriene diol

Isolated cembratrienediols may find a number of applications in smoking products and/or smokeless tobacco products. In some embodiments, isolated cembratriene diols are degraded by various means and the degradation products are used in smoking products and/or smokeless tobacco products. For example, in certain embodiments, isolated cembratriene diols and/or degradation products thereof may find use as tobacco-derived, natural flavor materials. In some embodiments, cembratriene diols and/or degradation products are used for therapeutic applications. For example, cembratriene diols have been found to provide potential health benefits in the treatment of cancer and certain neurodegenerative diseases. See, for example, Saito et al., Agric. Biol. Chem. 51(3): 941-43 (1987) and U.S. Pat. No. 4,701,570 to Mizusaki et al., which are incorporated herein by reference. Cembratriene diols and derivatives thereof may also be useful as drugs to prevent smoking and/or to treat nicotine addiction. See, for example, El Sayed et al., *Expert Opin. Invest. Drugs* 16(6): 877-87 (2007).

Sucrose esters are glycolipid compounds, characterized by low molecular weight carboxylic acids attached to hydroxide groups of the glucose portion of sucrose. Sucrose esters are considered to be some of the most important aroma and sensory precursors responsible for Oriental tobacco flavor. See, for example, Leffingwell et al., *Rec. Adv. Tob. Sci.* 14: 169-218 (1998), which is incorporated herein by reference.

Sucrose esters are typically sucrose molecules comprising three acyl groups on the glucose ring, each hydrocarbon chain of the acyl group comprising 3-8 carbon atoms and optionally including one or more double bonds. The sucrose esters also typically include an acetyl group on either the glucose ring or the fructose ring, which gives rise to the common reference to these esters as tetra-acyl sucrose esters. The exact structure of the sucrose esters isolated according to the present invention can vary somewhat as to placement, chain length, and saturation of the acyl groups, most sucrose esters of Oriental tobacco are encompassed by the following structure:

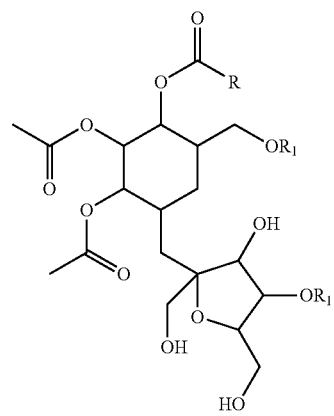

exemplary sucrose esters wherein each R is an independently selected C3-C8 hydrocarbon, which can be straight or branched and saturated or unsaturated, and both $R_1$ substituents are H or one $R_1$ is H and the other is acetyl (—C(O)CH$_3$). Most common R groups comprise butyl, pentyl, and hexyl.

Lutein is a major carotenoid pigment in tobacco.

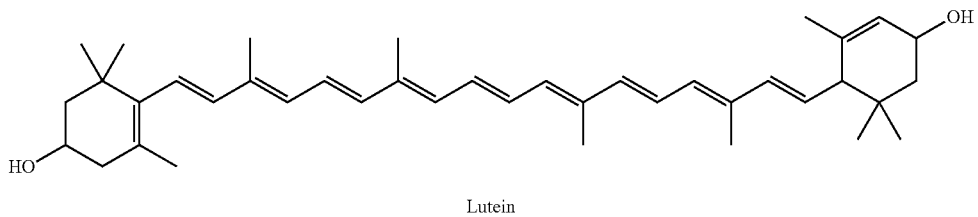 [SMILES: CC1=CC(O)CC(C)(C)C1/C=C/C(C)=C/C=C/C(C)=C/C=C/C=C(C)/C=C/C=C(C)/C=C/C1=C(C)CC(O)CC1(C)C]

Lutein

Lutein is known to break down during the air-curing of green tobacco to produce several ionones and derivatives thereof. Two important types of derivatives of lutein are megastigmatrienones and beta-damascenone. These compounds impact the aroma characteristics of cured tobacco. In addition to being degradation products of lutein, megastigmatrienone and beta-damascenone may also be separately extracted and isolated from tobacco according to the methods provided herein.

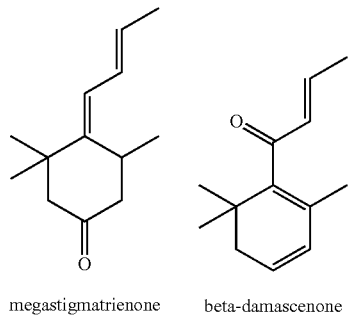

megastigmatrienone    beta-damascenone

Isolated lutein may find a number of applications in smoking products and/or smokeless tobacco products. In some embodiments, isolated lutein is degraded by various means and the degradation products produced therefrom can be used in smoking products and/or smokeless tobacco products. For example, in certain embodiments, isolated lutein and/or degradation products thereof may find use as tobacco-derived, natural flavor materials, colorants, or antioxidants. Lutein is also useful as a nutritional and/or therapeutic compound. See for example, Granado et al., *Br. J. Nutr.* 90(3): 487-502 (2003); Sies et al., *Int. J. Vitam. Nutr. Res.* 73(2): 95-100 (2003); and Krinsky et al., *Annu. Rev. Nutr.* 23(2): 171-201 (2003), which are incorporated herein by reference.

Solanone is a compound that is a useful tobacco flavorant and flavor enhancer. It is specifically noted to be present in burley tobacco aroma. See, for example, Domle et al., *Helv. Chim. Acta,* 55(6): 1866-1882 (1972), which is incorporated herein by reference. Although it is commonly produced by synthetic means (see, e.g., Johnson et al., *J. Org. Chem.* 30(9): 2918-2921 (1965); and U.S. Pat. No. 4,433,695 to Hall et al. and U.S. Pat. No. 4,547,594 to Light et al., which are incorporated herein by reference), solanone is present in tobacco and may be isolated according to the methods provided herein.

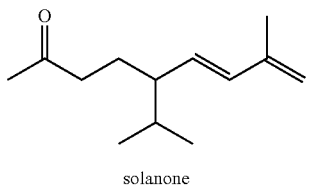

solanone

Isolated solanone may find a number of applications in smoking products and/or smokeless tobacco products. In some embodiments, isolated solanone may be degraded by various means and the degradation products may be used in smoking products and/or smokeless tobacco products. For example, in certain embodiments, isolated solanone and/or degradation products thereof may find use as tobacco-derived, natural flavor materials.

Neophytadiene is reported to be a tobacco flavor enhancer in that it may act as a flavor carrier by entrapping volatiles in the tobacco smoke aerosol. See, for example, J. C. Leffingwell, Leaf chemistry: basic chemical constituents of tobacco leaf and differences among tobacco types. Tobacco: Production, Chemistry and Technology, 265-284 (1999).

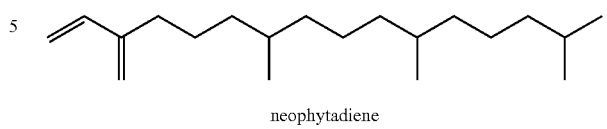

neophytadiene

Isolated neophytadiene may find a number of applications in smoking products and/or smokeless tobacco products. In some embodiments, isolated neophytadiene may be degraded by various means and the degradation products may be used in smoking products and/or smokeless tobacco products. For example, in certain embodiments, isolated neophytadiene and/or degradation products thereof may find use as tobacco-derived, natural flavor materials.

Norsolanadione is another compound that is known to be useful as a tobacco flavorant and in augmenting or enhancing the aroma and taste of smoking tobacco. Like solanone, this compound is commonly synthesized, rather than isolated. See, for example, U.S. Pat. No. 4,517,385 to Light et al., which is incorporated herein by reference.

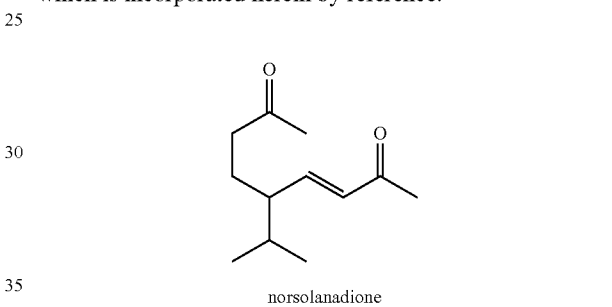

norsolanadione

Isolated norsolanadione may find a number of applications in smoking products and/or smokeless tobacco products. In some embodiments, isolated norsolanadione may be degraded by various means and the degradation products may be used in tobacco products. For example, in certain embodiments, isolated norsolanadione and/or degradation products thereof may find use as tobacco-derived, natural flavor materials.

Following extraction of compounds of interest from tobacco, it is desirable according to the present invention to further isolate and purify certain compounds. Because the extraction processes disclosed herein typically lead to complex mixtures of compounds, they must be further treated to provide desired mixtures of compounds and/or single isolated compounds (e.g., to give isolates comprising at least about 75% by weight of the compound or compounds).

The means by which such mixtures and/or single isolated compounds are provided can vary. Additional solvent extractions (e.g., solvent extraction using polar solvents, organic solvents, or supercritical fluids), chromatography, distillation, filtration, recrystallization, and/or solvent-solvent partitioning may be used to isolate and/or purify desired compounds from the extracts.

In some embodiments, multiple methods are used to isolate and/or purify the desired compounds. For example, solvent extraction may be combined with one or more chromatographic methods. The sample obtained via extraction may be dissolved in a solvent and injected directly onto the flash chromatography system or may be treated in some way prior to injection. In another example, in some embodiments, the sample is first treated to remove one or more compounds that are known to elute under similar conditions as the compound(s) to be isolated by flash chromatography. In one particular embodiment, an extract obtained by methanol extraction of a tobacco material is processed to remove quercetin-3-rutinoside ("rutin"). For example, the rutin can be removed from the extract by adding water, methanol, and methylene chloride to the extract and extracting the rutin into the methanol/water layer. The methylene chloride layer can be concentrated and further processed (e.g., by chromatography) to isolate and/or purify the desired compound(s) contained therein. In other embodiments, the extract can be dissolved and directly subjected to chromatographic separation.

In some embodiments, preparative liquid chromatography is used to isolate and/or purify certain compounds of interest from a tobacco extract. In some embodiments, a compound or compounds of interest are isolated using preparative liquid chromatography based on the elution times of standards. Various automated commercial prep-LC systems are available, from manufacturers including Waters, Agilent Technologies, and Bio-Rad. The specific parameters of the prep LC system used can be varied by one of skill in the art to achieve the desired level of resolution. For example, the solvent may be any solvent or mixture of solvents sufficient to dissolve the compound(s) of interest. The solvent may be, for example, water, methanol, ethanol, ethyl acetate, diethyl ether, methylene chloride, chloroform, petroleum ether, and/or hexanes. The system may be operated with an isocratic or gradient solvent system (i.e., varying the ratio of two or more solvents as a function of time). In some embodiments, the solvent system can be chosen such that it provides the best resolution between the compound of interest and other compounds present in the mixture. The flow rate of the system may be varied, for example, from about 10 mL/min to about 100 mL/min (e.g., about 36 mL/min).

In some embodiments, flash chromatography is used to isolate and/or purify certain compounds of interest from a tobacco extract. Flash chromatography systems are known in the art and exemplary systems are discussed, for example, in Still et al., J. Org. Chem. 42: 2923-2925 (1978) and U.S. Pat. No. 4,591,442 to Andrews, which are incorporated herein by reference. Various automated commercial flash chromatography systems are available, from manufacturers including Biotage, Teledyne Isco, Grace Davison Discovery Sciences, and Buchi. Flash chromatography may be desirable to provide reasonably large quantities of compound, as columns typically have relatively large particle sizes (e.g., roughly 30-40 μm) and can accommodate a greater quantity of sample (and a more concentrated sample), allowing more of the compound(s) of interest to be isolated per injection.

The specific parameters of the flash chromatography system used can be varied by one of skill in the art to achieve the desired level of resolution. For example, the solvent may be any solvent or mixture of solvents sufficient to dissolve the compound(s) of interest. The solvent may be, for example, water, methanol, ethanol, ethyl acetate, diethyl ether, methylene chloride, chloroform, petroleum ether, and/or hexanes. The system may be operated with an isocratic or gradient solvent system (i.e., varying the ratio of two or more solvents as a function of time). In some embodiments, the solvent system may be chosen to provide the best resolution between the compound of interest and other compounds present in the mixture. The flow rate of the system may be varied, for example, from about 20 to about 200 mL/min (e.g., about 150 mL/min).

Flash chromatography may or may not provide the compound(s) of interest at a sufficient purity level. In certain embodiments, the fractions corresponding to the compound(s) of interest may be collected, combined, and concentrated to give an isolate comprising the compound(s) of interest at a sufficient level of purity (i.e., wherein the compound(s) of interest are present in a sufficient weight percentage of the isolate). For example, the isolate of the present invention can comprise the compound(s) of interest in an amount of greater than about 75% by weight, greater than about 80% by weight, greater than about 85% by weight, greater than about 90% by weight, greater than about 95% by weight, greater than about 98% by weight, or greater than about 99% by weight. In some embodiments, fractions obtained from flash chromatography can be further resolved using preparative liquid chromatography.

In some embodiments, isolated compounds or mixtures thereof can be subjected to conditions so as to cause those compounds to undergo chemical transformation. For example, the tobacco material obtained from plants of the Nicotiana species or portion thereof can be treated to cause chemical transformation or be admixed with other ingredients. In some embodiments, the extracts obtained therefrom, or the isolated compound(s) (isolates) can be treated to cause chemical transformation or be admixed with other ingredients. The chemical transformations or modification of the tobacco material, extract, or isolated compound can result in changes of certain chemical and physical properties of the tobacco material, extract, or isolated compound(s) (e.g., the sensory attributes thereof). Exemplary chemical modification processes can be carried out by acid/base reaction, hydrolysis, oxidation, heating and/or enzymatic treatments; and as such, compounds can undergo various degradation reactions.

In certain embodiments, the tobacco material, extract, or isolate is treated to provide degradation products (e.g., lutein may be treated to provide various flavor compounds, including megastigmatrienones and/or β-damascenone; cis-abienol may be treated to provide sclareolide, sclareol, and/or ambroxide). Degradation products are any compounds that are produced from the compounds extracted and/or isolated according to the present invention. Degradation products can be formed naturally from such compounds or may be produced by an accelerated degradation process (e.g., by the addition of heat and/or chemicals to accelerate the breakdown of the compounds). These compounds can be degraded, for example, by means of oxidation (e.g., through treatment with $H_2O_2$ or other oxidizing agents) and/or hydrolysis reactions.

Exemplary types of further ingredients that can be admixed with the tobacco material, extracts, or isolates according to the present invention include one or more flavorants, fillers, binders, pH adjusters, buffering agents, colorants, disintegration aids, antioxidants, humectants and preservatives.

The extracts and isolates of the present invention are useful as components added to tobacco compositions, particularly tobacco compositions incorporated into smoking articles or smokeless tobacco products. Addition of the extracts or isolates to a tobacco composition can enhance the tobacco composition in a variety of ways, depending on the nature of the extract or isolate and the type of tobacco composition. Exemplary extracts and isolates can serve to provide flavor and/or aroma to a tobacco product (e.g., composition that alters the sensory characteristics of tobacco compositions or smoke derived therefrom). The extracts and isolates of the invention can also be used as components of tobacco products that contain no other tobacco material therein. In other words, the extract or isolate of the invention could be used as the sole source of tobacco in the tobacco product of the invention by, for example, incorporating the extract or isolate into an oral smokeless tobacco composition, such as a product adapted to dissolve or melt in the oral cavity.

The form of the extract or isolate obtained according to the present invention can vary. Typically, the isolate is in a solid, liquid, or semi-solid or gel form. The isolate can be used in concrete, absolute, or neat form. Solid forms of the isolate include spray-dried and freeze-dried forms. Liquid forms of the isolate include isolate contained within aqueous or organic solvent carriers.

The extract or isolate can be employed as a component of a tobacco composition in a variety of ways. The extract or isolate can be employed as a component of processed tobaccos. In one regard, the extract or isolate can be employed within a casing formulation for application to tobacco strip (e.g., using the types of manners and methods set forth in U.S. Pat. No. 4,819,668 to Shelar, which is incorporated herein by reference) or within a top dressing formulation. Alternatively, the extract or isolate can be employed as an ingredient of a reconstituted tobacco material (e.g., using the types of tobacco reconstitution processes generally set forth in U.S. Pat. No. 5,143,097 to Sohn; U.S. Pat. No. 5,159,942 to Brinkley et al.; U.S. Pat. No. 5,598,868 to Jakob; U.S. Pat. No. 5,715,844 to Young; U.S. Pat. No. 5,724,998 to Gellatly; and U.S. Pat. No. 6,216,706 to Kumar, which are incorporated herein by reference). The extract or isolate also can be incorporated into a cigarette filter (e.g., in the filter plug, plug wrap, or tipping paper) or incorporated into cigarette wrapping paper, preferably on the inside surface, during the cigarette manufacturing process.

The *Nicotiana*-derived extract or isolate can be incorporated into smoking articles. Representative tobacco blends, non-tobacco components, and representative cigarettes manufactured therefrom, are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,220,930 to Gentry; and U.S. Pat. No. 5,360,023 to Blakley et al.; US Pat. Application 2002/0000235 to Shafer et al.; and PCT WO 02/37990. Those tobacco materials also can be employed for the manufacture of those types of cigarettes that are described in U.S. Pat. No. 4,793,365 to Sensabaugh; U.S. Pat. No. 4,917,128 to Clearman et al.; U.S. Pat. No. 4,947,974 to Brooks et al.; U.S. Pat. No. 4,961,438 to Korte; U.S. Pat. No. 4,920,990 to Lawrence et al.; U.S. Pat. No. 5,033,483 to Clearman et al.; U.S. Pat. No. 5,074,321 to Gentry et al.; U.S. Pat. No. 5,105,835 to Drewett et al.; U.S. Pat. No. 5,178,167 to Riggs et al.; U.S. Pat. No. 5,183,062 to Clearman et al.; U.S. Pat. No. 5,211,684 to Shannon et al.; U.S. Pat. No. 5,247,949 to Deevi et al.; U.S. Pat. No. 5,551,451 to Riggs et al.; U.S. Pat. No. 5,285,798 to Banerjee et al.; U.S. Pat. No. 5,593,792 to Farrier et al.; U.S. Pat. No. 5,595,577 to Bensalem et al.; U.S. Pat. No. 5,816,263 to Counts et al.; U.S. Pat. No. 5,819,751 to Barnes et al.; U.S. Pat. No. 6,095,153 to Beven et al.; U.S. Pat. No. 6,311,694 to Nichols et al.; and U.S. Pat. No. 6,367,481 to Nichols, et al.; US Pat. Appl. Pub. No. 2008/0092912 to Robinson et al.; and PCT WO 97/48294 and PCT WO 98/16125. See, also, those types of commercially marketed cigarettes described *Chemical and Biological Studies on New Cigarette Prototypes that Heat Instead of Burn Tobacco*, R.J. Reynolds Tobacco Company Monograph (1988) and *Inhalation Toxicology*, 12:5, p. 1-58 (2000).

The extract or isolate described herein can be incorporated into smokeless tobacco products, such as loose moist snuff, loose dry snuff, chewing tobacco, pelletized tobacco pieces (e.g., having the shapes of pills, tablets, spheres, coins, beads, obloids or beans), extruded or formed tobacco strips, pieces, rods, cylinders or sticks, finely divided ground powders, finely divided or milled agglomerates of powdered pieces and components, flake-like pieces, molded processed tobacco pieces, pieces of tobacco-containing gum, rolls of tape-like films, readily water-dissolvable or water-dispersible films or strips (e.g., US Pat. App. Pub. No. 2006/0198873 to Chan et al.), or capsule-like materials possessing an outer shell (e.g., a pliable or hard outer shell that can be clear, colorless, translucent or highly colored in nature) and an inner region possessing tobacco or tobacco flavor (e.g., a Newtoniam fluid or a thixotropic fluid incorporating tobacco of some form). Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. App. Pub. Nos. 2005/0244521 to Strickland et al. and 2008/0196730 to Engstrom et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See also, the types of smokeless tobacco formulations, ingredients, and processing methodologies set forth in U.S. Pat. No. 6,953,040 to Atchley et al. and U.S. Pat. No. 7,032,601 to Atchley et al.; US Pat. Appl. Pub. Nos. 2002/0162562 to Williams; 2002/0162563 to Williams; 2003/0070687 to Atchley et al.; 2004/0020503 to Williams; 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

The amount of extract or isolate added to a tobacco composition, or otherwise incorporated within a tobacco composition or tobacco product, can depend on the desired function of that extract or isolate, the chemical makeup of that extract or isolate, and the type of tobacco composition to which the extract or isolate is added. The amount added to a tobacco composition can vary, but will typically range from about 5 ppm to about 5 weight percent based on the total dry weight of the tobacco composition to which the extract or isolate is added. The amount added may vary, depending, for example, on the goal to be achieved by addition of such compound or mixture of compounds (e.g., the enhancement of flavor) and on the specific characteristics of the compound or mixture of compounds to be added.

EXPERIMENTAL

Aspects of the present invention is more fully illustrated by the following examples, which are set forth to illustrate certain aspects of the present invention and are not to be construed as limiting thereof.

Example 1

Extraction and Isolation of Sucrose Esters, Lutein, Cembratrienediols and Cis-Abienol Extraction

*Nicotiana tabacum* Galpao tobacco is harvested, chopped into pieces, and extracted with methanol. The leaves are removed and the methanol extract is concentrated to approximately 77% solids by weight. The concentrated methanol extract separates into two layers, comprising an upper tar-like layer (which is soluble in methanol) and a lower aqueous layer (which is soluble in water). The upper tar-like layer is separated and is found to contain leaf surface analytes of interest such as sucrose esters, cembratrienediols, and cis-abienol. These analytes of interest can be separated and collected by liquid chromatography and/or flash chromatography.

Isolation Methods

Preparative scale liquid chromatography is commonly used to separate and collect compounds of interest in a complex mixture (e.g., using a Waters prep LC system comprising a Waters 2707 Autosampler, a Waters DAD detector, a Waters 2545 Quaternary Gradient Module, and a Waters Fraction Collector III and equipped with a Waters μBondapak C18 19×300 mm column and fraction collector).

Separation methods are typically developed on an analytical scale liquid chromatography column (e.g., using a Waters 2695 LC system equipped with a Waters μBondapak C18 3.9×300 mm 10 μm particle column) and scaled up to a preparative scale liquid chromatography system. Flash chromatography (e.g., using a Teledyne Isco CombiFlash Automated Flash Purification System with 275 g C18 Gold column) may also be used to isolate compounds of interest. This technique can be used alone or in tandem with preparative chromatography to isolate and collect various compounds.

Isolation of Sucrose Esters

Sucrose esters are isolated from the tar-like layer by preparative scale liquid chromatography. The tar-like mixture is dissolved in methanol (roughly 20 mg/mL) and injected (1 mL) on the Waters prep LC system noted above, operated at a flow rate of 36 mL/min, isocratic analysis with 75:25 methanol: water, and a Waters DAD detector at 214 nm. The fractions corresponding to the known retention time of sucrose ester standards (collected between about 1.0 and about 5.6 minutes) are collected and combined. Another major peak is noticed to elute with the sucrose esters at approximately 1.6 minutes. HR-LC-MS analysis of these fractions shows that this peak corresponds to quercetin-3-rutinoside or rutin. The concentration of rutin in the tar-like mixture as determined by HR-LC-MS analysis is approximately 800 μg/g.

To generate an extract free of the rutinoside, a liquid-liquid extraction is performed on the tar-like layer prior to prep LC. The tar-like layer (about 2 g) is dissolved in methanol (30 mL). This mixture is added to a reparatory funnel with distilled, deionized water (80 mL) and methylene chloride (40 mL). The mixture is shaken, the aqueous layer (shown to contain the rutin) is discarded, and the methylene chloride layer is removed and concentrated. The resulting material (reconstituted in methanol) is analyzed by HR-LC-MS, which showed the presence of sucrose esters but not the rutinoside. The rutinoside-free material is then injected onto the prep LC system to isolate the sucrose esters.

The fractions corresponding to the known retention time of sucrose ester standards are collected and combined. The combined fractions are concentrated to remove methanol and methylene chloride is added to the remaining water layer in a 1:1 ratio. The tubes are shaken, centrifuged, and the aqueous layer is discarded. The methylene chloride layer is concentrated and dissolved in isopropyl alcohol for HR-LC-MS analysis. The tar-like layer of tobacco methanol extract is determined to contain approximately 1,000 μg/g of a range of sucrose esters. This extract exhibits a similar qualitative distribution of sucrose esters as is present in other Oriental, cured tobacco types.

Isolation of Lutein

Lutein is isolated by prep LC from the tar-like layer, which is first treated to remove rutinoside, as described above. The rutinoside-free mixture is injected onto the prep LC system (10 mL injection volume) comprising a Symmetry Prep C18 19×300 mm 7 μm particle column at ambient temperature, operated at a flow rate of 26 mL/min, a solvent system of methanol and water, with initial ratio of 75:25, ratio at 10 minutes of 75:25, ratio at 15 minutes of 100:0, and ratio at 25 minutes of 75:25: water, and a Waters DAD detector at 443 nm. The fraction collector is set to collect 40 second fractions throughout the run, with total analysis time of 30 minutes. Lutein elutes at approximately 18.7 minutes under these conditions (as correlated with a lutein standard previously injected onto the prep LC system).

Lutein is also isolated from the tar-like layer by flash chromatography. A sample of the tar-like layer, which is first treated to remove rutinoside, as described above, is injected (15 mL injection volume) onto the flash chromatography system. The flash chromatography system is operated at a flow rate of 150 mL/min with a solvent (methanol and water) gradient with initial ratio of 75:25, ratio at 5 minutes of 75:25, ratio at 7 minutes of 100:0, and ratio at 15 minutes of 75:25, and a detector set at 443 nm. The fractions giving rise to a signal at 443 nm after the elution of cis-abienol were collected on the flash chromatography system, combined, and concentrated (e.g., using a Buchi Rotavapor unit set at 50° C. and a vacuum of 337 mBar). The combined, concentrated fractions are dissolved and injected onto the prep LC system (10 mL injection volume) comprising a Symmetry Prep C18 19×300 mm 7 μm particle column at ambient temperature, operated at a flow rate of 26 mL/min, a solvent system of methanol and water, with initial ratio of 75:25, ratio at 3 minutes of 75:25, ratio at 5 minutes of 100:0, and ratio at 12 minutes of 75:25: water, and a Waters DAD detector at 443 nm. The fraction collector is set to collect 20 second fractions throughout the run, with total analysis time of 15 minutes. Lutein elutes at 9 minutes.

Lutein-containing fractions that have been isolated by prep LC and/or flash chromatography are combined and concentrated to remove methanol (e.g., using a Buchi Rotovapor unit set at 50° C. and a vacuum of 337 mBar). The resulting material is a semi-solid form of lutein.

Isolation of Cembratrienediols

Cembratrienediols are isolated from the tar-like layer by preparative scale liquid chromatography. A sample of the tar-like layer described above, is injected (1 mL injection volume) onto the flash chromatography system. The flash chromatography system is operated at a flow rate of 36 mL/min with an isocratic solvent system (75:25 methanol: water) and a detector set at 214 nm. The fractions giving rise to a signal at 214 nm were collected on the flash chromatography system. The fraction collector is set to collect 20 second fractions throughout the run, with total analysis time of 10 minutes. Using the retention time of β-cembratrienediol and α-cembratrienediol standards, the fractions corresponding to each of these compounds were collected, and separately combined. On this system, the β-cembratrienediol is eluted at 9.0 minutes and the α-cembratrienediol is eluted at 6.9 minutes.

The isolated fractions are separately concentrated to remove methanol from the fractions, leaving aqueous solutions. Methylene chloride is added to each isolated fraction, the fractions are shaken to isolate the desired compound in the methylene chloride layer, and the fractions are centrifuged. The aqueous layer is discarded and the remaining methylene chloride layers are analyzed by GC/MS (e.g., using an Agilent 6890/5973 system from Agilent). GC/MS is conducted by adding DMF with internal standard (400 ppm tert-butyl hydroquinone) and BSTFA with 1% TMCS to vials containing the isolated fractions. The vials are kept at 76° C. for 30 minutes and cooled to room temperature for 30 minutes. The resulting solutions are analyzed by GC/MS, and peak identification is done by comparing the spectra of the silylated cembratrienediols with the spectra of known standards.

The mass spectra confirms that the combined fractions are the α and β cembratriene diols, and the data indicates that the both cembratrienediol fractions are approximately 99% pure based on the total area count. The β-cembratrienediol fraction contains a small amount of sugar-like compounds and hexadecanoic acid and the α-cembratrienediol fraction contains small amounts of sugar-like compounds and a phytol-like compound. The tar-like layer of tobacco methanol extract is determined to contain approximately 80 mg/g β-cembratrienediol and approximately 30 mg/g α-cembratrienediol.

Isolation of Cis-Abienol

Cis-abienol is isolated from the tar-like layer by preparative scale liquid chromatography. A sample of the tar-like layer is first treated to remove rutinoside, as described above. The rutinoside-free mixture is injected onto the prep LC system (10 mL injection volume) comprising a Symmetry Prep C18 19×300 mm 10 μm particle column at ambient temperature, operated at a flow rate of 36 mL/min, an isocratic solvent system of methanol and water, with ratio of 75:25, and a Waters DAD detector at 214 nm. The fraction collector is set to collect 20 second fractions throughout the run (of 12 mL each), with total analysis time of 20 minutes. Cis-abienol elutes at approximately 17.0 minutes under these conditions.

Initially, the isolated fractions with a significant absorption peak at 214 nm, are unknown. Thus, the combined fractions are analyzed by GC/MS, which is inconclusive. The isolated fraction is infused onto the Thermo TSQ Quantum Ultra MS/MS using an Atmospheric Pressure Chemical Ionization probe for ionization of the sample. This technique indicates that the molecular weight of the compound in the isolated fraction is 29 amu. The isolated fraction is additionally analyzed by UV/Vis spectroscopy (e.g., using a Hewlett Packard 8453 UV/Vis spectrophotometer), which shows a maximum absorption at 238 nm. Further confirmation of the identity of this isolated fraction is based on reported HPLC-ESI-MS molecular weight, NMR, and UV/Vis data on cis-abienol in an article by Ding et al., *Chromatographia* 66:529-532 (2007), which is incorporated herein by reference.

Cis-abienol is alternatively isolated from the tar-like layer by flash chromatography. A sample of the tar-like layer, which is first treated to remove rutinoside, as described above, is injected (15 mL injection volume) onto the flash chromatography system. The flash chromatography system is operated at a flow rate of 150 mL/min with a solvent (methanol and water) gradient with initial ratio of 75:25, ratio at 5 minutes of 75:25, ratio at 7 minutes of 100:0, and ratio at 15 minutes of 75:25, and a detector set at 214 nm. The fractions giving rise to a signal at 214 nm are collected on the flash chromatography system, combined, and concentrated (e.g., using a Buchi Rotavapor unit set at 50° C. and a vacuum of 337 mBar). The combined, concentrated fractions are dissolved and injected onto the prep LC system (10 mL injection volume) comprising a Symmetry Prep C18 19×300 mm 7 μm particle column at ambient temperature, operated at a flow rate of 26 mL/min, a solvent system of methanol and water, with initial ratio of 75:25, ratio at 10 minutes of 75:25, ratio at 15 minutes of 100:0, and ratio at 20 minutes of 75:25, and a Waters DAD detector at 214 nm. The fraction collector is set to collect 20 second fractions throughout the run (12 mL volume of each), with total analysis time of 30 minutes. Cis-abienol elutes at 17.8 minutes.

The cis-abienol fractions collected from the preparative LC and/or the flash chromatography method are concentrated to provide a semi-solid form of cis-abienol. High volume isolation and collection of cis-abienol are typically conducted on the flash chromatography system, which allows for greater efficiency, as more concentrated samples can be injected. In some cases, fractions from flash chromatography must be further resolved using preparative HPLC; however, flash chromatography typically provides sufficient resolution of cis-abienol without the need for preparative HPLC of the fractions.

Example 2

Extraction and Isolation of Sucrose Esters, Lutein, Cembratrienediols and Cis-Abienol A mixture of flue-cured, burley, and Oriental tobaccos is subjected to a dry steam distillation. Specifically, a strip blend of flue cured, burley, and Oriental tobaccos is placed in a 640 ft$^3$ wagon equipped with steam distillation capability Anhydrous steam is passed through the wagon and condensed, producing approximately 4 gallons per minute of steam distillate. The distillate is processed employing equipment traditionally employed for the isolation of peppermint oils. A few minutes after beginning the steam distillation process, an oil sheen begins to appear on the surface of the collected distillate. As time progresses, the sheen becomes a defined oil layer resting on top of the water condensate. This reddish-brown essential oil is gently removed from the water.

The essential oil is dissolved in methylene chloride and analyzed by gas chromatography/mass spectrometry (GC/MS, e.g., Agilent 6890 GC equipped with Agilent 5973 MSD). Data indicates that the essential oil comprises, as major volatile and semi-volatile compounds, solanone, neophytadiene, palmitic acid, and oleic acid. Other components of the essential oil are megastigmatrienone isomers, ionol derivatives, β-damascenone, and norsolanadione.

Further, the distillate water that was first passed through the essential oil isolation equipment and subsequently exhausted to the sewer (i.e., the "waste" stream) is captured. Samples of the "waste" stream collected during the distillation as a function of time are dissolved in methylene chloride and analyzed by GC/MS. The resulting chromatograms indicate that the "waste" stream contains a notable number of volatile and semi-volatile compounds including some of the compounds found in the essential oil (e.g., neophytadiene, nicotine, furfuryl alcohol, and bipyridine).

The "waste" stream is separated into aqueous and organic components to facilitate downstream processing/separation of the essential oil into less complex mixtures or individual components. Specifically, "waste" water from the steam distillation process is added to silica contained within a fritted glass cylinder. The water is gently removed from the silica using a water aspirator vacuum. Hexane is percolated through the column, followed by MTBE, followed by methanol. The organic solvents are removed by rotary evaporation and the resulting materials are reconstituted in methylene chloride. The methylene chloride samples are analyzed by GC/MS. The major component of the hexane extract is neophytadiene.

Example 3

Extraction and Isolation of Sucrose Esters and Cembratrienediols

A tobacco leaf is dipped into methylene chloride at room temperature for approximately 30 seconds. The resulting methylene chloride solution is concentrated and the extract is cleaned using a method described in Ashraf-Khorassani et al., *Beitrage Tabkforsch. Int.* 23: 32-45 (2008), which is incorporated herein by reference in its entirety.

The cleaned extract is purified with normal phase HPLC with UV detection at 214 nm, using a cyano-bonded silica column (25 cm×10 mm, $d_p$=5 μm) and a mobile phase of ethanol/iso-octane/water in a ratio of 15:85:0.1. Peaks are identified for sucrose esters, α-cembrene diol and β-cembrene diol; fractions corresponding to each peak are collected individually. The identities of the fractions corresponding to each peak are confirmed by GC-FID (MS), DB5, 15 m×0.25 mm (TMS derivatives) with an initial oven temperature of 80° C. (held for 2 minutes), which was ramped up 10° C./min to 140° C., ramped up 5° C./min to 300° C. and held at 300° C. for 10 minutes.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method of extracting and isolating compounds from plants of the *Nicotiana* species, comprising:
   receiving a plant material of the *Nicotiana* species;
   contacting the plant material with a solvent for a time and under conditions sufficient to extract one or more desired compounds from the plant material into the solvent;
   separating the solvent containing the one or more desired compounds from the extracted plant material; and
   purifying the solvent containing the one or more desired compounds to provide an isolate comprising at least about 75 percent by weight of the one or more desired compounds, the one or more desired compounds being selected from the group consisting of solanone, neophytadiene, megastigmatrienone, β-damascenone, norsolanadione, cis-abienol, α-cembratrienediol, β-cembratrienediol, lutein, degradation products thereof, and mixtures thereof,
   wherein the solvent is dry steam.

2. The method of claim 1, wherein the plant material of the *Nicotiana* species is provided in green form.

3. The method of claim 1, wherein the plant material of the *Nicotiana* species is provided in cured form.

4. The method of claim 1, wherein the plant material of the *Nicotiana* species is in a form selected from the group consisting of whole leaf, laminae, cut filler, volume expanded, stems, cut-rolled stems, cut-puffed stems, reconstituted tobacco, and particulate.

5. The method of claim 1, wherein the one or more desired compounds are selected from the group consisting of solanone, neophytadiene, megastigmatrienone, β-damascenone, and norsolanadione.

6. The method of claim 1, wherein the contacting step further comprises collecting a distillate.

7. The method of claim 6, wherein the distillate comprises a water layer and an oily layer.

8. The method of claim 7, wherein the solvent containing the one or more desired compounds is selected from the group consisting of the oily layer, the water layer, and a waste stream generated from the distillation process.

9. The method of claim 1, wherein the purifying step comprises using preparative scale liquid chromatography.

10. The method of claim 1, wherein the purifying step comprises using flash chromatography.

11. The method of claim 1, wherein the purifying step provides an isolate comprising greater than about 90% by weight of the one or more desired compounds.

12. The method of claim 1, wherein the purifying step provides an isolate comprising greater than about 95% by weight of the one or more desired compounds.

13. The method of claim 1, further comprising adding the isolate to a tobacco composition adapted for use in a smoking article or a smokeless tobacco composition.

14. The method of claim 1, further comprising treating the isolate to provide one or more degradation products therefrom, wherein the treating is selected from oxidation, heat treatment, and a combination thereof.

15. A method of extracting and isolating compounds from plants of the *Nicotiana* species, comprising:
   receiving a plant material of the *Nicotiana* species;
   contacting the plant material with a solvent for a time and under conditions sufficient to extract one or more desired compounds from the plant material into the solvent;
   separating the solvent containing the one or more desired compounds from the extracted plant material;
   purifying the solvent containing the one or more desired compounds to provide an isolate comprising at least about 75 percent by weight of the one or more desired compounds, the one or more desired compounds being selected from the group consisting of solanone, neophytadiene, megastigmatrienone, β-damascenone, norsolanadione, cis-abienol, α-cembratrienediol, β-cembratrienediol, lutein, degradation products thereof, and mixtures thereof; and
   treating the isolate to provide one or more degradation products therefrom, wherein the treating is selected from oxidation, heat treatment, and a combination thereof,
   wherein the isolate comprises lutein and wherein the one or more degradation products are selected from the group consisting of megastigmatrienone, beta-damascenone, and mixtures thereof, or
   wherein the isolate comprises cis-abienol and wherein the one or more degradation products are selected from the group consisting of sclareolide, sclareol, ambroxide, and mixtures thereof.

16. The method of claim 15, wherein the plant material of the *Nicotiana* species is in a form selected from the group consisting of whole leaf, laminae, cut filler, volume expanded, stems, cut-rolled stems, cut-puffed stems, reconstituted tobacco, and particulate.

17. The method of claim 15, wherein the plant material of the *Nicotiana* species is provided in green form.

18. The method of claim 15, wherein the plant material of the *Nicotiana* species is provided in cured form.

19. The method of claim 15, wherein the solvent is methanol.

20. The method of claim 15, wherein the purifying step comprises using preparative scale liquid chromatography.

21. The method of claim 15, wherein the purifying step comprises using flash chromatography.

22. The method of claim 15, wherein the purifying step provides an isolate comprising greater than about 90% by weight of the one or more desired compounds.

23. The method of claim 15, wherein the purifying step provides an isolate comprising greater than about 95% by weight of the one or more desired compounds.

24. The method of claim 13, wherein the isolate is added in the form of a casing formulation or a top dressing formulation applied to tobacco strip or in the form of a component of a reconstituted tobacco material.

25. The method of claim 13, wherein the tobacco composition comprises a tobacco material adapted for use in a smoking article.

26. The method of claim 25, wherein the amount of isolate in the tobacco composition is between about 5 ppm and about 5 weight percent based on the total dry weight of the tobacco material in the smoking article.

27. The method of claim 13, wherein the tobacco composition comprises a tobacco material adapted for use in a smokeless tobacco product.

28. The method of claim 27, wherein the amount of isolate in the tobacco composition is between about 5 ppm and about 5 weight percent based on the total dry weight of the tobacco material in the smokeless tobacco product.

29. The method of claim 15, further comprising:
adding the isolate to a tobacco composition adapted for use in a smoking article or a smokeless tobacco composition.

30. The method of claim 29, wherein the isolate is added in the form of a casing formulation or a top dressing formulation applied to tobacco strip or in the form of a component of a reconstituted tobacco material.

31. The method of claim 29, wherein the tobacco composition comprises a tobacco material adapted for use in a smoking article.

32. The method of claim 31, wherein the amount of isolate in the tobacco composition is between about 5 ppm and about 5 weight percent based on the total dry weight of the tobacco material in the smoking article.

33. The method of claim 29, wherein the tobacco composition comprises a tobacco material adapted for use in a smokeless tobacco product.

34. The method of claim 33, wherein the amount of isolate in the tobacco composition is between about 5 ppm and about 5 weight percent based on the total dry weight of the tobacco material in the smokeless tobacco product.

* * * * *